United States Patent
Harmer et al.

(10) Patent No.: US 6,593,505 B1
(45) Date of Patent: Jul. 15, 2003

(54) CATALYST OF MIXED FLUOROSULFONIC ACIDS

(75) Inventors: Mark A. Harmer, Kennett Square, PA (US); Eugene F. Hartstein, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/341,112

(22) Filed: Jan. 13, 2003

Related U.S. Application Data

(62) Division of application No. 09/606,276, filed on Jun. 29, 2000, now Pat. No. 6,395,673.

(51) Int. Cl.$^7$ .............................. C07C 2/08; C07C 5/25
(52) U.S. Cl. ...................... 585/526; 585/506; 585/507; 585/520; 585/527; 585/530; 585/531; 585/532; 585/533; 585/664; 585/668; 585/669; 585/670
(58) Field of Search ............................... 585/506, 507, 585/520, 526, 527, 530, 531, 532, 533, 664, 668, 669, 670

(56) References Cited

U.S. PATENT DOCUMENTS

| | | |
|---|---|---|
| 3,708,553 A | 1/1973 | Olah |
| 3,970,721 A | 7/1976 | Brockington et al. |
| 3,985,678 A | 10/1976 | Estes et al. |
| 4,008,178 A | 2/1977 | Brockington |
| 4,038,212 A | 7/1977 | Brockington et al. |
| 4,118,433 A | 10/1978 | Innes |
| 4,791,081 A | 12/1988 | Childress et al. ............. 502/62 |
| 5,220,095 A | 6/1993 | Hommeltoft et al. ........ 585/720 |
| 5,233,119 A | 8/1993 | Kallenbach et al. ........ 585/721 |
| 5,245,100 A | 9/1993 | Hommeltoft et al. ........ 585/720 |
| 5,284,993 A | 2/1994 | Eastman ..................... 585/842 |
| 5,288,685 A | 2/1994 | Kallenbach et al. ........ 502/168 |
| 5,292,986 A | 3/1994 | Abbott ........................ 585/730 |
| 5,326,922 A | 7/1994 | Huss, Jr. et al. ............. 585/722 |
| 5,349,116 A | 9/1994 | Kallenbach et al. ........ 585/730 |
| 5,414,187 A | 5/1995 | King et al. .................. 585/730 |
| 5,475,184 A | 12/1995 | Joly et al. ................... 585/730 |
| 5,491,278 A | 2/1996 | Augstadt et al. ............ 585/731 |
| 5,498,820 A | 3/1996 | Hommeltoft ................ 585/730 |
| 5,659,105 A | 8/1997 | Clerici et al. ............... 585/730 |
| 5,675,053 A | 10/1997 | Hommeltoft ................ 585/730 |
| 5,689,030 A | 11/1997 | Randolph ................... 585/724 |
| 5,723,715 A | 3/1998 | Randolph et al. ........... 585/724 |
| 5,731,256 A | 3/1998 | Benazzi et al. ............. 502/202 |
| 5,767,335 A | 6/1998 | Anderson et al. ........... 585/723 |
| 5,817,908 A | 10/1998 | Mehlberg ................... 585/716 |
| 5,824,622 A | 10/1998 | Harmer et al. .............. 502/407 |
| 5,841,014 A | 11/1998 | Graves et al. .............. 585/313 |
| 5,847,252 A | 12/1998 | Stine et al. ................. 585/330 |
| 5,849,978 A | 12/1998 | Benzaai et al. ............. 585/730 |
| 5,891,819 A | 4/1999 | Randolph et al. ........... 502/216 |
| 5,958,822 A | 9/1999 | Beckerbauer et al. ....... 502/168 |

FOREIGN PATENT DOCUMENTS

| | | |
|---|---|---|
| CA | 1020590 | 11/1977 |
| CA | 1125639 A | 7/1996 |
| CA | 1125640 | 7/1996 |
| EP | 605279 | 6/1994 |
| EP | 0 663 377 A1 | 7/1995 |
| EP | 761306 | 3/1997 |
| EP | 0839781 A1 | 5/1998 |
| EP | 0790 224 B1 | 4/1999 |
| GB | 2044628 A | 10/1980 |
| IT | 1272926 | 7/1997 |

Primary Examiner—Elizabeth D. Wood

(57) ABSTRACT

A catalyst comprising A) a stationary acid component selected from the group consisting of a perfluorinated ion exchange polymer on an inert support, a silane modified perfluorosulfonic acid, and a sulfated metal oxide; and B) a mobile acid component selected from the group consisting of chlorosulfonic acid, fluorosulfonic acid, a fluorinated monosulfonic acid, a fluorinated sulfonimide, a fluorinated disulfonic acid, and an adjunct acid mixture is disclosed.

16 Claims, No Drawings

CATALYST OF MIXED FLUOROSULFONIC ACIDS

This application is A Divisional of Ser. No. 09/606,276, filed Jun. 29, 2000, now U.S. Pat. No. 6,395,673.

BACKGROUND OF THE INVENTION

In the oil refining industry, the term "alkylation" is used to describe processes in which isoparaffins (e.g., isobutane) are reacted with olefin (e.g., 1-butene) to form the "alkylate" or higher molecular weight branched paraffins (typically isooctane or 2,2,4-trimethylpentane in the isobutane/1-butene case). The higher molecular weight branched paraffins produced have desirable high research octane numbers, making the product an excellent blending component for gasoline. Typically, in the example reaction described, a large excess of the 1-butene is used to drive olefin conversion, and the excess isobutane is recovered and recycled.

An important alkylation method is an acid-catalyzed process. Concentrated sulfuric acid and more recently, hydrofluoric acid have been used as the catalyst. However, there has been continuing interest in the development of a solid cata lyst to replace sulfuric and hydrofluoric acids.

A solid-supported liquid catalyst in a moving catalyst zone, through which the alkane/alkene stream can pass, has been reduced to practice by, for instance, Hommeltoft and Topsoe in U.S. Pat. No. 5,245,100, who describe a catalyst of trifluoromethanesulfonic acid (triflic acid $CF_3SO_3H$) adsorbed on, inter alia, silica. As the loading is reduced with the Hommeltoft and Topsoe catalyst system, the useful lifetime of the catalyst system decreases sharply to impracticably short time periods.

Clerici, et al., in U.S. Pat. No. 5,659,105, describe an alkylation catalyst composed of a silica-based material having surface Si—OH groups esterified with a linear perfluorosulfonic acid of the formula $CF_3(CF_2)_nSO_3H$, where n is 0–11. Clerici, et al., asserted the catalyst showed higher activity than the triflic acid adsorbed on silica described by Hommeltoft and Topsoe. However, the esterified —Si—OH groups are not stable and are removed from the silica in use.

A further problem is the tendency for the acid catalysts to become deactivated or passified, a process believed to be associated with the formation of stable esters between the strong acid and the feedstock olefin. While such passivation occurs with stationary acid catalysts, the effect is minimized by the flow-through, recovery, and recycle associated with mobile catalysts. Hommeltoft, et al., in Ind. Eng. Chem. Res. 1997, 36, 3491–3497, provide a discussion of such passivation mechanisms. Hommeltoft, et al., report that while the addition of a mobile Lewis acid such as boron trifluoride, antimony pentafluoride, or aluminum chloride does improve the lifetime of the stationary catalyst, it also introduces handling problems with the volatile and hazardous Lewis acid. It is desirable to minimize the mobile acid throughput and recycle.

The catalyst of the present invention provides economies over the sulfuric acid process and a marked reduction in process hazards over the hydrofluoric acid process. Additionally, the catalyst of this invention provides a longer catalyst life over both the acid modified silica and the mobile acid supports of the prior art. By comparison with the mobile acid treated supports of the prior art, the amount of mobile acid required is substantially reduced.

SUMMARY OF THE INVENTION

The present invention comprises a catalyst comprising A) a stationary acid component selected from the group consisting of a perfluorinated ion exchange polymer on an inert support, a silane modified perfluorosulfonic acid, and a sulfated metal oxide; and B) a mobile acid component selected from the group consisting of chlorosulfonic acid, fluorosulfonic acid, a fluorinated monosulfonic acid of Formula 1a, a fluorinated sulfonimide of Formula 1b or 1c, a fluorinated disulfonic acid of Formula 2, and an adjunct acid mixture; wherein Formula 1a is $R^1—CF_2—SO_3H$,
Formula 1b is $(R^1—CF_2—SO_2)_2NH$,
Formula 1c is $R^1—CF_2—SO_2—NH—R^2$, wherein each $R^1$ is independently Cl; F; H; branched or straight chain $C_1$ to $C_{10}$ alkyl optionally interrupted by oxygen atoms and optionally substituted with Cl or F; $C_6$ to $C_{12}$ aryl; or $C_6$ to $C_{12}$ aryl substituted with up to two groups selected from the group consisting of Cl, F, $C_1$ to $C_{10}$ alkyl, and $C_1$ to $C_{10}$ alkoxy;

each $R^2$ is independently branched or straight chain $C_1$ to $C_{10}$ alkyl optionally interrupted by oxygen atoms and optionally substituted with Cl or F; $C_6$ to $C_{12}$ aryl; or $C_6$ to $C_{12}$ aryl substituted with up to two groups selected from the group consisting of Cl, F, $C_1$ to $C_{10}$ alkyl, and $C_1$ to $C_{10}$ alkoxy; and Formula 2 is $HSO_3—CF_2—R^3—CF_2—SO_3H$ wherein $R^3$ is a divalent $C_1$ to $C_{10}$ alkylene optionally interrupted by oxygen atoms and optionally substituted with Cl or F; a $C_6$ to $C_{12}$ arylene; or $C_6$ to $C_{12}$ arylene substituted with up to two groups selected from the group consisting of Cl, F, $C_1$ to $C_{10}$ alkyl, and $C_1$ to $C_{10}$ alkoxy.

The present invention further comprises an improved alkylation process wherein the improvement comprises reacting an olefin with an alkane in the presence of a catalyst as described above.

The present invention further comprises an improved process for isomerization of at least one alkene wherein the improvement comprises conducting the isomerization in the presence of a catalyst as described above.

The present invention further comprises an improved process for oligomerization of an olefin wherein the improvement comprises conducting the oligomerization in the presence of a catalyst as described above.

The present invention is directed toward an improved catalyst that comprises a new combination of a fixed solid strong acid (hereinafter the "stationary acid", "stationary acid component", "heterogeneous acid" or "heterogeneous acid component") and a mobile strong acid (hereinafter the "mobile acid", "mobile acid component", "homogeneous acid" or "homogeneous acid component"), and the use of the catalyst in alkylation, oligomerization, and isomerization processes. The catalyst of this invention substantially reduces the concentration of homogeneous acid required in the heterogeneous acid component, thus minimizing the amount of eluted homogeneous acid requiring recovery and recycle.

Specifically, the stationary acid component of this invention comprises (a) a highly fluorinated polymeric sulfonic acid fixed on or entrapped within a porous silica or metal oxide support, (b) a silane-modified perfluorosulfonic acid on silica or metal salts, or (c) a sulfated metal oxide.

In the first embodiment, the stationary acid is a perfluorinated ion-exchange polymer containing pendant sulfonic acid groups dispersed and entrapped within a silica or metal oxide support. Examples of such stationary acid components are a solid acid component such as the NAFION perfluorinated ion-exchange polymer in a silica nanocomposite, as described by Harmer and Sun in U.S. Pat. No. 5,824,622, or a perfluorosulfonic acid grafted on silica as described by Harmer et al. in U.S. Pat. No. 5,958,822 in which the graft is

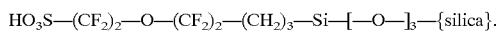

Perfluorinated ion-exchange polymers (PFIEP) containing pendant sulfonic acid, carboxylic acid, or sulfonic acid and carboxylic acid groups used in the present invention are well known compounds. See, for example, Waller et al., Chemtech, July 1987, pp. 438–441, and references therein, and U.S. Pat. Nos. 5,094,995 and 5,824,622. Perfluorinated ion-exchange polymers (PFIEP) containing pendant carboxylic acid groups also have been described in U.S. Pat. No. 3,506,635. Polymers discussed by J. D. Weaver et al., in Catalysis Today, 14 (1992) 195–210, are also useful in the present invention. Polymers that are suitable for use in the present invention have structures that include a substantially fluorinated carbon chain that may have attached to it side chains that are substantially fluorinated. In addition, these polymers contain sulfonic acid groups or derivatives of sulfonic acid groups, carboxylic acid groups or derivatives of carboxylic acid groups and/or mixtures of these groups. For example, copolymers of a first fluorinated vinyl monomer and a second fluorinated vinyl monomer having a pendant cation exchange group or a pendant cation exchange group precursor can be used, e.g., sulfonyl fluoride groups ($-SO_2F$) which can be subsequently hydrolyzed to sulfonic acid groups. Possible first monomers include tetrafluorbethylene (TFE), hexafluoropropylene, vinyl fluoride, vinylidene fluoride, trifluoroethylene, chlorotrifluoroethylene, perfluoro (alkyl vinyl ether), and mixtures thereof. Possible second monomers include a variety of fluorinated vinyl ethers with pendant cation exchange groups or precursor groups. Preferably, the polymer contains a sufficient number of acid groups to give an equivalent weight of from about 500 to 20,000, and most preferably from 800 to 2,000. Representative of the perfluorinated polymers for use in the present invention are NAFION PFIEP (a family of polymers for use in the manufacture of industrial chemicals, commercially available from E. I. du Pont de Nemours and Company), and polymers, or derivatives of polymers, disclosed in U.S. Pat. Nos. 3,282,875; 4,329,435; 4,330,654; 4,358,545; 4,417,969; 4,610,762; 4,433,082; and 5,094,995. More preferably the polymer comprises a perfluorocarbon backbone and a pendant group represented by the formula $-OCF_2CF(CF_3)OCF_2CF_2SO_3X$, wherein X is H in the practice of this invention. Polymers and alkali metal or ammonium salts of polymers of this type are disclosed in U.S. Pat. No. 3,282, 875.

Typically, such perfluorinated polymers are derived from sulfonyl group-containing polymers having a fluorinated hydrocarbon backbone chain to which are attached the functional groups or pendant side chains which in turn carry the functional groups. Fluorocarbosulfonic acid catalyst polymers useful in the practice of this invention have been made by Dow Chemical and are further described in Catalysis Today, 14 (1992) 195–210. Other perfluorinated polymer sulfonic acid catalysts are described in Synthesis, G. I. Olah, P. S. Iyer, G. K. Surya Prakash, 513–531 (1986).

There are also several additional forms of the above polymer catalysts in which the sulfonic acid group is present as a metal salt in the microcomposite of the present invention. These comprise 1) a partially cation-exchanged polymer, 2) a completely cation-exchanged polymer, and 3) a cation-exchanged polymer where the metal cation is coordinated to another ligand (see U.S. Pat. No. 4,414,409, and F. J. Waller in British Polymer Journal, Volume 16, pp. 239–242; and ACS Symposium Series 308; American Chemical Society, Washington, DC, 1986, Chapter 3). The metal cations useful in these additional forms of the above polymer catalysts are $Cr^{3+}$, $Sn^{2+}$, $Al^{3+}$, $Fe^{3+}$, $Co^{2+}$, $Zn^{2+}$, $Hg^{2+}$, and lanthanides such as Y.

Preferred PFIEP suitable for use in the present invention comprise those containing sulfonic acid groups. Most preferred is a sulfonated NAFION PFIEP.

Typically, such PFIEP materials do not have satisfactory physical properties for them to be used in a fixed bed catalyst column. A more suitable fixed bed form is obtained when the PFIEP is entrapped and highly dispersed within a silica or metal oxide network, wherein the weight percentage of perfluorinated ion-exchange polymer in the microcomposite is from about 0.1 to 90 percent, preferably from about 5 to about 80 percent, most preferably from about 5 to about 20 percent and wherein the size of the pores in the microcomposite is about 0.5 nm to about 75 nm. The terms "organic-inorganic polymer microcomposite" or "microcomposite" are used to describe this structure.

The organic-inorganic polymer microcomposites of the present invention are high surface area, porous microcompositions that exhibit excellent catalytic activity. Whereas the surface area of NAFION nm 50 PFIEP, a commercial product, is approximately 0.02 $m^2$ per gram, a preferred embodiment of the present invention comprises microcomposites of PFIEP and silica having a surface area typically of 5 to 500 $m^2$ per gram. The composition of the present invention exists as a particulate solid that is porous and glass-like in nature, typically 0.1–4 mm in size and structurally hard, similar to dried silica gels. The perfluorinated ion exchange polymer (PFIEP) is highly dispersed within and throughout the silica network of the microcomposite of the present invention, and the microstructure is very porous. The porous nature of this material is evident from the high surface areas measured for these glass-like pieces, having typical pore diameters in the range of 1–25 nm. Another preferred embodiment is the use of the present invention in pulverized form.

Within the composite, silica is preferred but a metal oxide can be substituted in place of the silica. The term "metal oxide" signifies metallic or semimetallic oxide compounds, including, for example, alumina, silica, titania, germania, zirconia, alumino-silicates, zirconyl-silicates, chromic oxides, germanium oxides, copper oxides, molybdenum oxides, tantalum oxides, zinc oxides, yttrium oxides, vanadium oxides, and iron oxides. The term "metal oxide precursor" refers to the form of the metal oxide that is originally added in the sol-gel process to finally yield a metal oxide in the final microcomposite. In the case of silica, for example, it is well known that a range of silicon alkoxides can be hydrolyzed and condensed to form a silica network. Such precursors as tetramethoxysilane (tetramethyl orthosilicate), tetraethoxysilane (tetraethyl orthosilicate), tetrapropoxysilane, tetrabutoxysilane, and any compounds under the class of metal alkoxides which in the case of silicon is represented by $Si(OR)_4$, where R includes methyl, ethyl, n-propyl, iso-propyl, n-butyl, sec-butyl, iso-butyl, tert-butyl or where R is a range of organic groups, such as alkyl. Also included, as a precursor form is silicon tetrachloride. Further precursor forms comprise organically modified silica, for example, $CH_3Si(OCH_3)_3$, $PhSi(OCH_3)_3$, and $(CH_3)_2Si(OCH_3)_2$. Other network formers include metal silicates, for example, potassium silicate, sodium silicate, lithium silicate. K, Na or Li ions can be removed using a DOWEX cation exchange resin (sold by Dow Chemical, Midland, Mich., which generates polysilicic acid that gels at slightly acid to basic pH. The use of LUDOX colloidal silica (E. I. du Pont de Nemours and Company, Wilmington, Del.) and fumed silica (CAB-O-SIL sold by Cabot Corporation of Boston, Mass.), which can be gelled by altering pH and adjusting the concentration in solution, will also yield a metal oxide network in the microcomposite of the invention. For example, typical precursor forms of silica are $Si(OCH_3)_4$, $Si(OC_2H_5)_4$ and $Na_2SiO_3$; and a typical precursor form of alumina is aluminum tri-sec-butoxide $Al(OC_4H_9)_3$.

In a second embodiment of the present invention, the stationary acid component of the catalyst is a silane-modified perfluorosulfonic acid as described by Harmer et al. in Chemical Communications, 1997, 1803–1804. Specifically, the stationary acid is a perfluorosulfonate/trisilanol having the structure $M^{30}$ $^-O_3S$—$(CF_2)_2$—O—$(CF_2)_2$—$(CH_2)_3$—Si—$[$—O—$]_3$—{silica}. The hydrolyzed alkoxysilane groups are attached to a silica support as described in the preceding reference and in Example 2 below.

In a third embodiment of the present invention, the stationary acid component of the catalyst is sulfated zirconia. Sulfated zirconia is described by Corma and Garcia in Organic Reactions Catalyzed over Solid Acids, in Catalysis Today, 38, 257–308, 1997, in which see Section 5, Sulfated Zirconia as a Solid Acid Catalyst, pp. 294–300. Other sulfated metal oxides useful in the practice of the third embodiment are sulfated $TiO_2$, $Fe_2O_3$, $Al_2O_3$, $SiO_2$, and $Bi_2O_3$.

The mobile acid component of the present invention comprises (a) chlorosulfonic acid, fluorosulfonic acid, or a fluorinated sulfonic acid or sulfonimide; (b) a fluorinated disulfonic acid; or (c) an adjunct acid mixture.

The first embodiment of the mobile acid component of the catalyst of this invention is selected from chlorosulfonic acid, fluorosulfonic acid, a fluorinated sulfonic acid of the structure of Formula 1a, or a fluorinated sulfonimide of the structure of Formula 1b or 1c:

| | |
|---|---|
| Cl-SO₃H | Chlorosulfonic acid |
| F-SO₃H | Fluorosulfonic acid |
| R¹—CF₂—SO₃H | Formula 1a |
| (R¹—CF₂—SO₂)₂NH | Formula 1b |
| R¹—CF₂—SO₂—NH—R² | Formula 1c | wherein
  each $R^1$ is independently Cl; F; H; branched or straight chain $C_1$ to $C_{10}$ alkyl or substituted $C_1$ to $C_{10}$ alkyl fully or partially substituted independently with chlorine and fluorine, the carbon chain of which is optionally interrupted by oxygen atoms; a $C_6$ to $C_{12}$ aryl; or $C_6$ to $C_{12}$ aryl substituted by up to two groups selected from Cl, F, $C_1$ to $C_{10}$ alkyl, and $C_1$ to $C_{10}$ alkoxyl.
  each $R^2$ is independently branched or straight chain $C_1$ to $C_{10}$ alkyl or substituted $C_1$ to $C_{10}$ alkyl fully or partially substituted independently with chlorine and fluorine, the carbon chain of which is optionally interrupted by oxygen atoms; a $C_6$ to $C_{12}$ aryl; or $C_6$ to $C_{12}$ aryl substituted by up to two groups selected from Cl, F, $C_1$ to $C_{10}$ alkyl, and $C_1$ to $C_{10}$ alkoxyl.

A preferred mobile acid of the structure of Formula 1a is triflic acid, $CF_3SO_3H$, bp 161° C. Most preferred is 1,1,2,2-tetrafluoroethanesulfonic acid, H—$CF_2$—$CF_2$—$SO_3H$, bp 245° C.

Higher molecular weight mobile acids have progressively diminished volatility and thus facilitate removal of the mobile acid from the product. However, in practice this is offset by the increase in equivalent weight and the need to have a higher weight loading of mobile acid on the support as the equivalent weight increases.

Other examples of Formula 1a useful in the present invention include the linear perfluoroalkane sulfonic acids $CF_3(CF_2)_nSO_3H$ wherein n is 1–12 and incompletely perfluorinated sulfonic acids such as 2-chloro-1,1,2-trifluoroethanesulfonic acid, CHClF—$CF_2$—$SO_3H$.

Examples of fluoroether sulfonic acids of Formula 1a useful herein are:

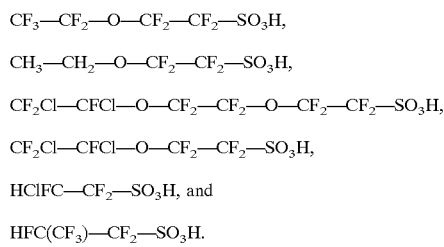

Examples of the sulfonimides of Formula 1b useful herein are $(CF_3$—$SO_2)_2$=NH, $CF_3SO_2NHSO_2C_3F_8$, and $(C_4F_9SO_2)_2NH$ and others as described by Ilmar et al. in "The Gas Phase Acidities of Very Strong Neutral Bronsted Acids," J. Am. Chem. Soc. 1994, 116, 3047–3057. Examples of the sulfonimides of Formula 1c useful herein are $CF_3$—$SO_2$—NH—$SO_2$—$CH_3$ and $CF_3$—$SO_2$—NH—$SO_2C_6H_5$.

A second embodiment of the mobile acid component of the catalyst of this invention is a perfluorinated or highly fluorinated disulfonic acid of the structure of Formula 2:

wherein
  $R^3$ is a divalent $C_1$ to $C_{10}$ alkylene or substituted $C_1$ to $C_{10}$ alkylene fully or partially substituted independently with chlorine and fluorine, the carbon chain of which is optionally interrupted by oxygen atoms; a $C_6$ to $C_{12}$ arylene; or $C_6$ to $C_{12}$ arylene substituted by up to two groups selected from Cl, F, $C_1$ to $C_{10}$ alkyl, and $C_1$ to $C_{10}$ alkoxyl.

Examples of the disulfonic acids of Formula 2 are $HSO_3$—$(CF_2)_n$—$SO_3H$ where n is 3–12, and $HO_3S$—$CF_2$—$CF_2$—O—$CF_2$—$CF_2$—$SO_3H$.

The mobile acids of Formulae 1a, 1b, 1c, and 2 are made according to methods known in the art.

A third embodiment of the mobile acid component of the catalyst of this invention is adjunct acid mixtures (Bronsted/Lewis acid mixtures) such as $HF/SbF_5$; $HSO_3F/SbF_5$; $CF_3SO_3H/SbF_5$; $HCF_2CF_2SO_3H/SbF_5$; the $SbF_5$ adjunct acid mixtures with the other mobile acids of Formulae 1a, 1b, 1c, and 2; and the corresponding compounds in which arsenic, niobium, or tantalum replaces the antimony. These compounds, known as "superacids", are further described by Olah, et al., in Superacids, John Wiley & Sons, New York N.Y., see particularly pp. 7–11.

The stationary and mobile acid components are combined for use in the practice of this invention. In the practice of the present invention, the stationary acid is packed under anhydrous conditions into a column, equipped with temperature measurement and control systems, a means to supply a feed stock (such as a 90% butane/10% 1-butene mixture for an alkylation run) at a controlled rate, and a means to collect and analyze the effluent gas stream. Typically, analysis is by gas chromatography. The efficacy of the catalyst system, and the lifetime of the catalyst prior to deactivation, is measured in terms of the conversion of the olefin. In laboratory scale experiments, eluted mobile acid is conveniently trapped in a small bed of convenient base, such as sodium carbonate, prior to analysis. In larger scale experiments provision for trapping and recycling the mobile acid is provided. The eluted mobile acids are recovered and recycled by methods well known in the art, such as by aqueous extraction, removal of the water by distillation, and finally isolating the anhydrous mobile acid by distillation from concentrated sulfuric acid. The column is further provided with a means to inject accurately the mobile acid into the inlet end of the column. The amount of the mobile acid injected is conveniently described in terms of acid equivalents of mobile acid per acid equivalent of the stationary acid. The range is 100:1 to 0.01:1 equivalents mobile acid:equivalent stationary acid and preferably 10:1 to 0.1:1 equivalents mobile acid:equivalent stationary acid.

The present invention further comprises the use of the catalyst in alkylation, isomerization, and oligomerization processes. An example of an alkylation process is the economically very important reaction of isobutane and 1-butene to give isooctanes. An example of an oligomerization process is the conversion of propylene to $C_6$ and $C_9$ products. Catalysis of olefin oligomerization is described in detail by A. Corma in "Inorganic Solid Acids and Their Use in Acid-Catalyzed Hydrocarbon Reactions," in Chem. Rev 1995, 95, 559–614). Examples of isomerization processes are the conversion of 1-butene to 2-butene and of alpha-olefins to internal olefins. Catalysis of $\alpha$-olefin isomerization is described by M. A. Harmer, W. E. Farneth, and Q. Sun in "Towards the Sulfuric Acid of Solids," in Advanced Materials, p. 1255–1257, 1998).

The terms "catalyst lifetime" and "time to deactivation" describe the time during which the catalyst acts effectively. For the purposes of this invention and the examples and comparative examples of this invention, catalyst lifetimes are compared using the time the catalyst is capable of producing an olefin conversion of 50% or greater. Such comparisons are made using the same feed composition, feed rate, column size and configuration, and column operating conditions.

The practice of this invention is now described by a specific example. A liquid phase mixture of 1-butene:i-butane (weight ratio 9:1) is passed through a vertical column containing a bed of the acid-containing modified silica or acid-entrapped silica, where 0.009 mL triflic acid per gram of the stationary acid bed has been applied to the inlet end of the column. This corresponds to 0.56 equivalents mobile acid/equivalent of stationary acid. The feed rate is 3 g of the 1-butene/i-butane mixture per gram of catalyst bed. The catalyst bed is operated at ambient temperature and 200 psig (1480 kPa). The product stream shows 100% conversion of the 1-butene to $C_5$–$C_9$ alkylation products, principally the $C_8$ product, 2,2,4-trimethylpentane. Triflic acid eluted from the column is trapped in a sodium carbonate trap. The catalyst life is approximately 5 hours. The catalyst is reactivated by reapplying a fresh portion of triflic acid to the inlet end of the catalyst bed, thus demonstrating a simulation of a continuous process in which the mobile acid component is fed continuously into the stationary acid bed with the hydrocarbon fee at a rate sufficient to maintain the desired ratio of equivalents of mobile acid to equivalent of stationary acid. The eluted mobile acid is recovered, purified as necessary, and reintroduced to the column by methods known to those skilled in the art and, for example by aqueous extraction of the product stream, distillation to concentrate the mobile acid, and finally distillation from concentrated sulfuric acid to recover anhydrous mobile acid.

In a continuous modification of the process of this invention, triflic acid is fed with the alkane/alkene stream, at a rate sufficient to maintain catalytic activity, and recovered from the product stream by methods well known to those skilled in the art. For instance, Hommeltoft and Topsoe in EP 0 433 954 B1, for instance, describe a method for the recovery of triflic acid involving the steps of aqueous extraction, distillation, and finally distilling the triflic acid in the presence of concentrated sulfuric acid. Recovered triflic acid is then reinjected into the column in the liquid feed stream.

The catalyst of the present invention provides economies over prior art sulfuric acid processes and a marked reduction in process hazards over prior art hydrofluoric acid processes. Additionally, the catalyst of this invention provides a longer catalyst life over both the acid modified silica and the mobile acid supports of the prior art. By comparison with the mobile acid treated supports of the prior art, the amount of mobile acid required is substantially reduced.

MATERIALS

The following materials are used in the Examples hereinafter:

1,1,2,2-tetrafluoroethanesulfonic acid is prepared from sodium hydrogen sulfate and tetrafluoroethane as described in U.S. Pat. No. 2,403,207.

NAFION, a perfluorinated ion exchange polymer, is available from E. I. du Pont de Nemours and Co., Wilmington Del. The preparation of a 13 wt % NAFION in silica (for Example 1) is given by Fraile, et al., in "Bis(oxazoline)-Copper Complexes, supported by Electrostatic Interactions, as Heterogeneous Catalysts for Enantioselective Cyclopropanation Reactions: Influence of the Anionic Support," in J. Catal., 186, 214–221 (1999). The NAFION silica catalyst is also commercially available as NAFION SAC 13 from E. I. du Pont de Nemours and Company in Wilmington Del.

Triflic acid, trifluoromethylsulfonic acid, is available from Aldrich Chemicals, Milwaukee Wis.

Silane-modified silica: The preparation of the acid-modified silica for Example 2 used Silica 60 and the procedure cited in Chem. Comm., 1997, 1803–1804, "Unique silane modified perfluorosulfonic acids as versatile reagents for new solid acid catalysts." This procedure is also described by Harmer, et al., in U.S. Pat. No. 5,958,822.

Silica was obtained from Aldrich Chemicals, Milwaukee Wis. Silica 60, (Aldrich 28,863–2), 70–230 mesh (28–90 cm^-1), about 500 m2/g surface area.

Sulfated zirconia was supplied by Magnesium Elektron, Inc. (MEI) as a commercial sample. The material was heated at 600° C. for 2 hours before use.

EXAMPLES

Example 1

An acid-modified silica stationary acid component was prepared using silica and a perfluorosulfonic acid (10.8 g) according to the method of Fraile, et al. (See MATERIALS, NAFION, above). Specifically, the NAFION solution is available commercially (Aldrich, Milwaukee Wis., NAFION perfluorinated ion-exchange resin, #27,470-4) as a 5 wt % solution in mixed alcohols and water. This is converted to a 3 wt % solution in water by repeatedly adding water and evaporating the diluted solution on a rotary evaporator to remove the alcohol. Typically, 100 g of water is added to 100 g of the 5 wt % alcohol solution. The volume is then reduced to about 165 mL under vacuum, which removes most of the alcohol. More water is added and the volume is reduced to 165 mL and the process repeated three times to give an approximate 3 wt % NAFION solution in water. 200 g of a 10 wt % silica-containing solution, made by diluting a sodium silicate solution, was added to 100 g of a 3 wt % aqueous NAFION-containing solution. The two solutions were mixed for 5 min. Approximately 52 g of 3.5M HCl was added to adjust the pH to 7. The system gelled in about 10–15 sec. The gel was dried at 90° C. overnight and re-acidified by repeated washing with 25 wt % nitric acid. The typical surface area was 200 m$^2$/g and the particle size about 1–3 mm. The loading of the NAFION, determined by the number of acid sites, was about 13 wt %. The particles were ground using a mortar and pestle and were fractionated, and the fraction of 70–230 mesh (28–91/cm) was used as the stationary acid component after drying.

A stainless steel column (about 35 cm in length and 8 mm in internal diameter) was packed with a layer of glass wool, a layer of anhydrous sodium carbonate (to absorb exiting mobile acid), and a second layer of glass wool at the bottom. The column was then loaded in a dry box with 10.8 g of the stationary acid component described above. The stationary acid component had been dried at 150° C. for 4 h in vacuum. The solid was packed by tapping gently and then 0.1 mL of triflic acid was applied to the top of the stationary acid component (the inlet end for the hydrocarbon feed) using a syringe. Glass wool was then placed on top of the solid/triflic material.

The packed column was inverted and attached to a liquid phase reactor, constructed of stainless steel, with inlet tubing for the preliquified isobutane/1-butene (8:1 by weight) mixture at the bottom and an outlet at the top. The outlet was connected to a back pressure regulator which in turn could be directed either to a gas chromatograph (GC) for product analysis or the product could be connected in a glass vessel, chilled with solid carbon dioxide, on the outlet. The reaction was monitored periodically (about every 20 min.) to measure the conversion of butene/isobutane to octane via the in-line GC.

The reactor temperature was set to 24° C. and the reactants were fed in to the reactor at 30 cc/hr. The system pressure was at 80 psig (655 kPa). After running for 45 min., the GC showed very little olefin (1-butene) remaining and the main product observed (equivalent to >95% of the 1-butene) was isooctane. The percentage conversion versus time is shown in Table 1.

Example 2

In Example 2 the stationary acid catalyst was the silane-modified perfluorosulfonic acid catalyst prepared as described by Harmer et al. in Chemical Communications, 1997, 1803–1804 (cited above). Specifically, the perfluoroiodide $ICF_2CF_2OCF_2CF_2SO_2F$ (213 g, available from the Shanghai Institute of Organic Chemistry, Academica Sinica, PR China) was stirred under nitrogen with allyl acetate (57 g) and heated to 100° C. Benzoyl peroxide (4 g) was added over 4 h. The solution was distilled to yield 200 g of pure product, $CH_3COOCH_2CHICH_2(CF_2)_2O(CF_2)_2SO_2F$, bp 87° C. at 0.1 mm Hg (13 Pa). 19F NMR data were as in the reference.

The product was added to isopropyl alcohol (35 mL), acetic acid (42 mL), and zinc powder (54.4 g) at 90° C. The mixture was left for a further 4 h. The residue was washed with water and aqueous sodium hydrogen carbonate solution. Distillation gave 108 g of pure $CH_2=CHCH_2(CF_2)_2O(CF_2)_2SO_2F$.

17.1 g of $CH_2=CHCH_2(CF_2)_2O(CF_2)_2SO_2F$ was added to 12.2 mL of triethoxysilane, $(EtO)_3SiH$, in 15 mL of toluene using 16 drops of an hydrosilation catalyst, platinum divinyltetramethyldisiloxane complex available from Gelest, Tullytown Pa. The reaction was left to stir at ambient temperature for three days. The product was distilled at 54° C. at 0.05 mm Hg to give the pure product. 3 g of the product $[(EtO)_3SiCH_2CH_2CH_2(CF_2)_2O\ (CF_2)_2SO_2F]$ was stirred with 1.09 g of potassium hydroxide in 4.56 g of water and left at 90–100° C. overnight. The solution was cooled in an ice bath and 4.5 g of DOWEX HCR-W2, (available from Aldrich, Milwaukee Wis.) was added with 1.5 g of water. After filtering off the resin the cold solution was added to 8.4 g of silica gel 70–230 mesh (28–91/cm) and the modified silica gel was heated at 100° C. overnight. Finally, the solid was treated with 25 wt % nitric acid at 65° C. for 4 hr followed by washing with distilled water until neutral. The product was then dried under vacuum at 120° C. overnight.

In Example 2, the stationary catalyst was packed into a stainless steel column having an inner diameter of 8 mm and a length of 35 cm. Dry potassium carbonate (5 g) was loaded at the bottom of column for each run to prevent acid from contaminating the GC analysis during each run. The packing procedure was otherwise as in Example 1 and included the addition of triflic acid onto the top of the column as described in Example 1. The column was packed with 7–8 mL of the dried silane-modified perfluorosulfonic acid catalyst prepared as described above.

A feed stream of preliquified isobutane/1-butene (8:1 by weight) was passed upward under a pressure of ca. 80–100 psig (655–793 kPa) at a rate of 30 mL/h at ambient temperature through the reactor. Product was analyzed as in Example 1 and the percentage conversion versus time is shown in Table 1.

Comparative Example A

This experiment was carried out using the procedure of Example 1, except that triflic acid is preapplied to a bed of silica without fluorinated sulfonic acid modification. The catalyst life was only about 1 hour.

The liquid isobutane/1-butene mixture was passed through the reactor loaded with unmodified silica (8 g) to which 0.1 mL triflic acid had been applied using the same flow rate and conditions as in Example 1. This amount of triflic acid was below the activity threshold stated in European Patent 433954A1 describing liquid mobile acid alkylation on silica support. Product alkylation was poor, showing zero conversion after one hour.

Comparative Example B

This experiment was carried out using the procedure of Example 1, except that the fluorosulfonic acid modified silica was used without the preapplication of the triflic acid. The catalyst life was less than 2 hours.

A perfluorosulfonic acid-modified silica stationary acid component was prepared according to the procedure described in Example 1, and was ground into a powder before use. The catalyst was used for alkylation as described in Example 1, without added triflic or 1,1,2,2-tetrafluoroethanesulfonic acid. The liquid isobutane/1-butene mixture was passed through the reactor using the same flow rate and conditions as in Example 1. Product alkylation was poor, remaining active for less than 2 hr.

Comparative Example C

A perfluorosulfonic acid-modified silica stationary acid component was prepared, ground, and packed into a column according to the procedure of Example 1. The catalyst was used for alkylation as described in Example 2, without added triflic acid. The liquid 1-butane/1-butene mixture was passed through the reactor with the same flow rate and conditions as Example 2. Product alkylation was poor, remaining active for less than 80 min.

TABLE 1

% Conversion vs. Time for Examples 1 and 2 and Comparative Examples A, B, and C.

| Time | Conversion % for Examples | | Conversion % for Comparative Examples | | |
|---|---|---|---|---|---|
| | Example 1 | Example 2 | Example A | Example B | Example C |
| 0' 20" | — | — | — | — | 10 |
| 0' 40" | — | — | 80 | 80 | — |
| 0' 45" | — | — | — | — | 7 |
| 1' 0" | — | — | 0 | — | — |
| 1' 30" | — | 91 | — | — | — |
| 2' 0" | — | 90 | — | 45 | — |
| 2' 5" | — | — | — | — | 5 |
| 2' 10" | 100 | — | — | — | — |
| 2' 30" | — | 90 | — | — | — |
| 2' 35" | 98 | — | — | 25 | — |
| 2' 55" | — | 82 | — | — | — |
| 3' 0" | 85 | — | — | 10 | — |
| 3' 45" | — | 70 | — | — | — |
| 4' 0" | 65 | 53 | — | 0 | — |
| 5' 0" | — | 30 | — | — | — |
| 5' 30" | 55 | — | — | — | — |
| 6' 0" | <50 (~25%) | — | — | — | — |

Table 1 shows the superior performance of the NAFION/silica/triflic acid catalyst of Example 1 in terms of both conversion and catalyst lifetime. The silane-modified perfluorosulfonic acid catalyst/triflic acid catalyst of Example 2 was almost as effective. Comparative Examples A (silica/triflic acid) and B (solid) acid from Example 1, PFEIP modified silica) and C (solid acid from Example 2) show sharply less conversion and catalyst lifetime.

Example 3

The procedure of Example 1 was operated until the catalyst was deactivated. A second 0.1-mL aliquot of triflic acid was charged to the bottom of the column and the alkylation resumed. Conversion after 2 hours was 95%. Example 3 showed the effect of the combination of the stationary and mobile acid components of the catalyst of this invention.

Comparative Example D

The procedure of Example 2 was repeated except that the catalyst was sulfated zirconia, predried at 150° C. for 3 hours, and not modified with a mobile perfluorosulfonic acid. Catalyst activity lasted 2 hours, and alkylation quality by GC analysis was inferior. Catalyst performance is shown in Table 2.

Example 4

The procedure of Comparative Example D using sulfated zirconia as the stationary acid was followed until the catalyst was inactive after 2 hours. Triflic acid (0.1 mL) was charged to the top of the column and the alkylation resumed and continued for 3 hours. Catalyst performance is shown in Table 2.

TABLE 2

% Conversion vs. Time for Example 4 and Comparative Example D.

| Time | Conversion % for Comparative Example D | Conversion % for Example 4 |
|---|---|---|
| 1' | 85 | 99 |
| 1' 30" | 55 | 85 |
| 1' 50" | 30 | — |
| 2' | — | 58 |

Table 2 shows significantly improved conversion and catalyst lifetime for Example 4 (where triflic acid was added to regenerate catalytic activity in a sulfated zirconia column that had become deactivated) versus the initial performance of the sulfated zirconia column (Comparative Example D).

Comparative Example E

The triflic acid modified silica was made via the U.S. Pat. No. 5,659,105 according to the following procedure. Triflic acid (1 mL) was added to 11 mL of silica gel (70–230 mesh, 28–91/cm) and the material was placed in a sealed tube (35-mL) with a TEFLON stopper. The tube and contents were heated to 150° C. for 2 days after which time the material was transferred and stored in dry box.

The silica containing triflic acid material (approximately 7.5 mL) was loaded on to a glass column, which has an 8×295 mm bed size, in a dry box. The column and contents were removed from the box and a mixture of 2-methylbutane and 1-pentene (12.5:1, 540 mL) was applied down the column at about 1 mL per minute. Some heat was felt on the column. The solution was passed down the column and any eluted acid collected with the product coming out of the bottom of the column. The solution from the bottom of the column was titrated against 0.2M NaOH to measure any eluted acid. It was found that about 84% of the acid was eluted from the column after about 100 mL of the 2-methylbutene/1-pentane mixture was passed down the column.

Comparative Example E showed that the alkylation catalyst of Clerici, et al., described in U.S. Pat. No. 5,659,105, contains esterified -Si—OH groups that are removed from the silica in use.

What is claimed is:

1. An improved process for isomerization of at least one alkene wherein the improvement comprises conducting the isomerization in the presence of a catalyst comprising A) a heterogeneous acid component selected from the group consisting of a perfluorinated ion exchange polymer on an inert support, a silane modified perfluorosulfonic acid on a support, and a sulfated metal oxide; and B) a homogeneous acid component selected from the group consisting of chlorosulfonic acid, fluorosulfonic acid, a fluorinated monosulfonic acid of Formula 1a, a fluorinated sulfonimide of Formula 1b or 1c, a fluorinated disulfonic acid of Formula 2, and an adjunct acid mixture which is 1) a Bronsted/Lewis acid mixture wherein the Bronsted acid is selected from the group consisting of HF, $HSO_3F$, $CF_3SO_3H$, and $HCF_2CF_2SO_3H$ and the Lewis acid is selected from the group consisting of $SbF_5$, $AsF_5$, $NbF_5$, and $TaF_5$ or 2) a mixture of said Bronsted/Lewis acid mixture with a compound of Formula 1a, Formula 1b or Formula 1c; wherein Formula 1a is $R^1—CF_2—SO_3H$,
Formula 1b is $(R^1—CF_2—SO_2)_2NH$,
Formula 1c is $R^1—CF_2—SO_2—NH—R^2$, wherein each $R^1$ is independently Cl, F, H, branched or straight chain $C_1$ to $C_{10}$ alkyl optionally interrupted by oxygen atoms and optionally substituted with Cl or F, $C_6$ to $C_{12}$ aryl, or $C_6$ to $C_{12}$ aryl substituted with up to two groups selected from the group consisting of Cl, F, $C_1$ to $C_{10}$ alkyl, and $C_1$ to $C_{10}$ alkoxy;

each $R^2$ is independently branched or straight chain $C_1$ to $C_{10}$ alkyl optionally interrupted by oxygen atoms and optionally substituted with Cl or F, $C_6$ to $C_{12}$ aryl, or $C_6$ to $C_{12}$ aryl substituted with up to two groups selected from the group consisting of Cl, F, $C_1$ to $C_{10}$ alkyl, and $C_1$ to $C_{10}$ alkoxy; and Formula 2 is $HSO_3$—$CF_2$—$R^3$—$CF_2$—$SO_3H$ wherein $R^3$ is a divalent $C_1$ to $C_{10}$ alkylene optionally interrupted by oxygen atoms and optionally substituted with Cl or F, a $C_6$ to $C_{12}$ arylene, or $C_6$ to $C_{12}$ arylene substituted with up to two groups selected from the group consisting of Cl, F, $C_1$ to $C_{10}$ alkyl, and $C_1$ to $C_{10}$ alkoxy.

2. The process of claim 1 wherein the heterogeneous acid component is a perfluorinated ion exchange polymer containing pendant sulfonic acid groups, pendant carboxylic acid groups, or a mixture thereof, on a silica or metal oxide support, or in a silica nanocomposite.

3. The process of claim 1 wherein the heterogeneous acid component is a perfluorosulfonic acid grafted on silica.

4. The process of claim 1 wherein the heterogeneous acid component is a sulfated metal oxide wherein the metal oxide is selected from the group consisting of $ZrO_2$, $TiO_2$, $Fe_2O_3$, $Al_2O_3$, $SiO_2$ and $Bi_2O_3$.

5. The process of claim 1 wherein the homogeneous acid component is triflic acid or 1,1,2,2-tetrafluoroethanesulfonic acid.

6. The process of claim 1 wherein the homogeneous acid component is $HSO_3$—$(CF_2)_n$—$SO_3H$ or $HO_3S$—$CF_2$—$CF_2$—$O$—$CF_2$—$CF_2$—$SO_3H$.

7. The process of claim 1 wherein the heterogeneous acid component is a perfluorinated ion exchange polymer containing pendant sulfonic acid groups, pendant carboxylic acid groups, or a mixture thereof, on a silica or metal oxide support or in a silica nanocomposite and the homogeneous acid component is triflic acid or 1,1,2,2-tetrafluoroethanesulfonic acid.

8. The process of claim 1 wherein the perfluorinated ion exchange polymer contains a pendant group represented by the formula —$OCF_2CF(CF_3)OCF_2CF_2SO_3H$.

9. An improved process for oligomerization of an olefin wherein the improvement comprises conducting the oligomerization in the presence of a catalyst comprising A) a heterogeneous acid component selected from the group consisting of a perfluorinated ion exchange polymer on an inert support, a silane modified perfluorosulfonic acid on a support, and a sulfated metal oxide; and B) a homogeneous acid component selected from the group consisting of chlorosulfonic acid, fluorosulfonic acid, a fluorinated monosulfonic acid of Formula 1a, a fluorinated sulfonimide of Formula 1b or 1c, a fluorinated disulfonic acid of Formula 2, and an adjunct acid mixture which is 1) a Bronsted/Lewis acid mixture wherein the Bronsted acid is selected from the group consisting of HF, $HSO_3F$, $CF_3SO_3H$, and $HCF_2CF_2SO_3H$ and the Lewis acid is selected from the group consisting of $SbF_5$, $AsF_5$, $NbF_5$, and $TaF_5$ or 2) a mixture of said Bronsted/Lewis acid mixture with a compound of Formula 1a, Formula 1b or Formula 1c; wherein Formula 1a is $R^1$—$CF_2$—$SO_3H$, Formula 1b is $(R^1$—$CF_2$—$SO_2)_2NH$, Formula 1c is $R^1$—$CF_2$—$SO_2$—$NH$—$R^2$, wherein each $R^1$ is independently Cl, F, H, branched or straight chain $C_1$ to $C_{10}$ alkyl optionally interrupted by oxygen atoms and optionally substituted with Cl or F, $C_6$ to $C_{12}$ aryl, or $C_6$ to $C_{12}$ aryl substituted with up to two groups selected from the group consisting of Cl, F, $C_1$ to $C_{10}$ alkyl, and $C_1$ to $C_{10}$ alkoxy;

each $R^2$ is independently branched or straight chain $CP_1$ to $C_{10}$ alkyl optionally interrupted by oxygen atoms and optionally substituted with Cl or F, $C_6$ to $C_{12}$ aryl, or $C_6$ to $C_{12}$ aryl substituted with up to two groups selected from the group consisting of Cl, F, $C_1$ to $C_{10}$ alkyl, and $C_1$ to $C_{10}$ alkoxy; and Formula 2 is $HSO_3$—$CF_2$—$R^3$—$CF_2$—$SO_3H$ wherein $R^3$ is a divalent $C_1$ to $C_{10}$ alkylene optionally interrupted by oxygen atoms and optionally substituted with Cl or F, a $C_6$ to $C_{12}$ arylene, or $C_6$ to $C_{12}$ arylene substituted with up to two groups selected from the group consisting of Cl, F, $C_1$ to $C_{10}$ alkyl, and $C_1$ to $C_{10}$ alkoxy.

10. The process of claim 9 wherein the heterogeneous acid component is a perfluorinated ion exchange polymer containing pendant sulfonic acid groups, pendant carboxylic acid groups, or a mixture thereof, on a silica or metal oxide support, or in a silica nanocomposite.

11. The process of claim 9 wherein the heterogeneous acid component is a perfluorosulfonic acid grafted on silica.

12. The process of claim 9 wherein the heterogeneous acid component is a sulfated metal oxide wherein the metal oxide is selected from the group consisting of $ZrO_2$, $TiO_2$, $Fe_2O_3$, $Al_2O_3$, $SiO_2$ and $Bi_2O_3$.

13. The process of claim 9 wherein the homogeneous acid component is triflic acid or 1,1,2,2-tetrafluoroethanesulfonic acid.

14. The process of claim 9 wherein the homogeneous acid component is $HSO_3$—$(CF_2)_n$—$SO_3H$ or $HO_3S$—$CF_2$—$CF_2$—$O$—$CF_2$—$CF_2$—$SO_3H$.

15. The process of claim 9 wherein the heterogeneous acid component is a perfluorinated ion exchange polymer containing pendant sulfonic acid groups, pendant carboxylic acid groups, or a mixture thereof, on a silica or metal oxide support or in a silica nanocomposite and the homogeneous acid component is triflic acid or 1,1,2,2-tetrafluoroethanesulfonic acid.

16. The process of claim 9 wherein the perfluorinated ion exchange polymer contains a pendant group represented by the formula —$OCF_2CF(CF_3)OCF_2CF_2SO_3H$.

* * * * *